(12) United States Patent
Senft et al.

(10) Patent No.: US 8,899,098 B2
(45) Date of Patent: Dec. 2, 2014

(54) SEMICONDUCTOR GAS SENSOR AND METHOD FOR MEASURING A RESIDUAL GAS PROPORTION WITH A SEMICONDUCTOR GAS SENSOR

(71) Applicant: Micronas GmbH, Freiburg (DE)

(72) Inventors: Christoph Senft, Munich (DE); Stefan Simon, Munich (DE); Walter Hansch, Mitterfels (DE)

(73) Assignee: Micronas GmbH, Freiburg (DE)

(*) Notice: Subject to any disclaimer, the term of this patent is extended or adjusted under 35 U.S.C. 154(b) by 258 days.

(21) Appl. No.: 13/683,235

(22) Filed: Nov. 21, 2012

(65) Prior Publication Data
US 2013/0139570 A1 Jun. 6, 2013

(30) Foreign Application Priority Data

Nov. 21, 2011 (DE) .................. 10 2011 118 931

(51) Int. Cl.
| | | |
|---|---|---|
| G01N 7/00 | (2006.01) | |
| H01L 29/66 | (2006.01) | |
| G01N 27/00 | (2006.01) | |
| G01N 27/414 | (2006.01) | |
| G01N 33/00 | (2006.01) | |

(52) U.S. Cl.
CPC .............. H01L 29/66 (2013.01); G01N 27/00 (2013.01); G01N 27/4143 (2013.01); G01N 33/004 (2013.01)
USPC ....................................................... 73/31.06

(58) Field of Classification Search
USPC ....................................................... 73/31.06
See application file for complete search history.

(56) References Cited

U.S. PATENT DOCUMENTS

| 6,041,643 | A | 3/2000 | Stokes et al. |
| 6,890,422 | B1 | 5/2005 | Stanglmeier et al. |
| 8,056,394 | B2 | 11/2011 | Frerichs et al. |
| 8,226,892 | B2 | 7/2012 | Wilbertz et al. |
| 2006/0246636 | A1* | 11/2006 | Imai et al. ................ 438/149 |
| 2009/0087639 | A1* | 4/2009 | Li et al. .................. 428/304.4 |
| 2011/0114914 | A1* | 5/2011 | Numata et al. .............. 257/9 |
| 2011/0318889 | A1* | 12/2011 | Chida ..................... 438/158 |

FOREIGN PATENT DOCUMENTS

| DE | 199 12 100 A1 | 10/2000 |
| EP | 1 079 229 A1 | 2/2001 |
| EP | 2 105 732 A1 | 9/2009 |
| EP | 2 105 734 A1 | 9/2009 |

* cited by examiner

Primary Examiner — Hezron E Williams
Assistant Examiner — Rodney T Frank
(74) Attorney, Agent, or Firm — Muncy, Geissler, Olds & Lowe, P.C.

(57) ABSTRACT

A semiconductor gas sensor is provided that has a gas-sensitive gate electrode separated by a gap from a channel region and is embodied as a suspended gate field effect transistor or the gate electrode is arranged as a first plate of a capacitor with gap and a second plate of the capacitor is connected to a gate of the field effect transistor embodied as capacitively controlled and the gate electrode has a conductive carrier layer with a bearing adhesion promoter layer and a gas-sensitive layer bearing on the adhesion promoter layer, wherein the gate electrode as a gas-sensitive layer has a platinum/gold alloy with a gold proportion in a range of 1% to 20% and a polymer layer with a thickness of less than 100 nm is embodied on the surface of the platinum/gold alloy and the gap is filled with an oxygen-free gas mixture.

11 Claims, 2 Drawing Sheets

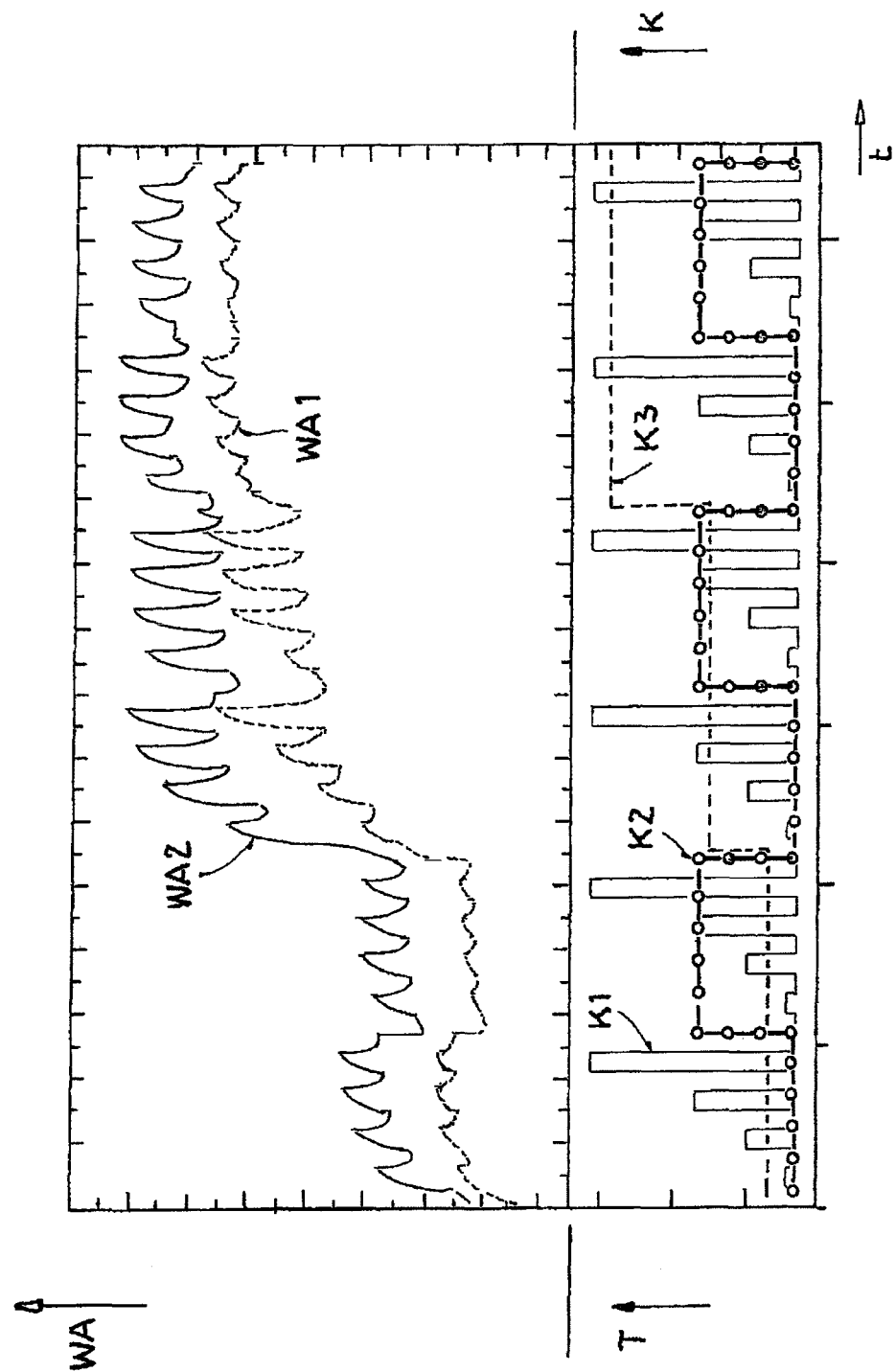

SEMICONDUCTOR GAS SENSOR AND METHOD FOR MEASURING A RESIDUAL GAS PROPORTION WITH A SEMICONDUCTOR GAS SENSOR

This nonprovisional application claims priority under 35 U.S.C. §119(a) to German Patent Application No. 10 2011 118 931.2, which was filed in Germany on Nov. 21, 2011, and which is herein incorporated by reference.

BACKGROUND OF THE INVENTION

1. Field of the Invention

The present invention relates to a semiconductor gas sensor and to a method for measuring a residual gas proportion with a semiconductor gas sensor.

2. Description of the Background Art

DE 199 12 100 A1, which corresponds to U.S. Pat. No. 6,890,422, discloses an electrochemical gas sensor, which responds to oxidizable gas components such as CO, for example, and hereby however does not catalytically change the establishment of equilibrium of a gas mixture that contains oxygen. A platinum/gold alloy with a gold proportion in a range between 0.5% to 20%, preferably with a gold proportion of 10% is used for the measuring electrode. The operating temperature of the sensor is approximately 500° C.

A semiconductor gas sensor embodied as an HSGFET (Hybrid Suspended Gate FET) for the detection of ozone is known from the printed publication "M. Zimmer et al., Gold and platinum as ozone sensitive layer in work-function gas sensors, sensors and actuators, B80 (2001) 174-178." It has been shown that a platinum electrode has no sensitivity to carbon monoxide. In contrast to the electrochemical sensors, with the HSGFET sensors or the SGFET sensors a detection of gases takes place via a change of the work function at the gas-sensitive layer. Sensors of this type are operated in general far below 500° C.

SUMMARY OF THE INVENTION

It is therefore an object of the invention to provide a semiconductor gas sensor that further develops the conventional art.

According to an embodiment of the invention, a semiconductor gas sensor, preferably equipped for a determination of carbon monoxide, is provided on the basis of a field effect transistor, which has a gas-sensitive gate electrode separated by a gap from a channel region and is embodied as a suspended gate field effect transistor, or the gate electrode is arranged as a first plate of a capacitor with gap and a second plate of the capacitor is connected to a gate of the field effect transistor embodied as capacitively controlled and the gate electrode has a semiconductor carrier layer or metallically conductive carrier layer with a bearing adhesion promoter layer and a gas-sensitive layer bearing on the adhesion promoter layer and the surface of the gas-sensitive layer faces towards the channel region or the second plate, wherein the gate electrode as a gas-sensitive layer has a platinum/gold alloy with a gold proportion in a range of 1% to 20% and a polymer layer with a thickness of less than 100 nm is embodied on the surface of the platinum/gold alloy and the gap is filled with a low-oxygen or oxygen-free gas mixture. It should be noted that a low-oxygen gas mixture is understood to mean a gas mixture the oxygen proportion of which in volume is less than 0.1%.

According to an embodiment of the invention, a method for measuring a residual gas proportion with a semiconductor gas sensor on the basis of a field effect transistor is provided, wherein the field effect transistor has a gas-sensitive gate electrode separated by a gap from a channel region and is embodied as a suspended gate field effect transistor (SGFET), or the gate electrode is arranged as a first plate of a capacitor with gap and a second plate of the capacitor is connected to a gate of the field effect transistor (CCFET) embodied as capacitively controlled, and the gate electrode has a semiconductor carrier layer or metallically conductive carrier layer with a bearing adhesion promoter layer and a gas-sensitive layer bearing on the adhesion promoter layer, and the surface of the gas-sensitive layer faces towards the channel region or the second plate, wherein the gas-sensitive layer is embodied a platinum/gold alloy with a gold proportion in a range of 1% to 20% and a polymer layer with a thickness of less than 100 nm is embodied on the surface of the platinum/gold alloy and an oxygen-free gas mixture is fed to the gate electrode and the residual gas proportion is enriched with carbon monoxide and the level of the proportion of carbon monoxide is determined.

It should be noted that the level of the proportion of carbon monoxide results with the method or the device according to the invention from the level of the voltage change at the gate electrode. Furthermore, compared to an electrochemical gas sensor, the semiconductor gas sensor with a detection of gas proportions operates according to a completely different operating principle. Instead of a chemical or catalytic reaction with an electrochemical gas sensor, in the case of the semiconductor gas sensor gases are detected in a physical manner by means of a determination of the work function change. A composition of a gas-sensitive layer cannot be transferred hereby from one type of sensor to the other type of sensor. Through the change in the work function at the gas-sensitive layer of the semiconductor gas sensor, a modulation of properties of the field effect transistor (FET for short) by means of the gate electrode takes place depending on the level of the carbon monoxide proportion. To put it another way, with the different levels of proportions of carbon monoxide, the conductivity of the channel region is modulated, i.e., with the SGFET the gate electrode operates as a gate, while with the CCFET the gate electrode modulates the conductivity of the channel region indirectly by means of a second plate, which is connected to the gate of the field effect transistor lying at a distance.

An advantage is that by means of the semiconductor gas sensor in an oxygen-free environment the proportion of carbon monoxide in a gas mixture can be determined reliably and in a simple manner. In contrast to an electrochemical sensor, according to the prior art, in which by means of a reactive oxidizing process and temperatures above 400° C. oxygen are necessary, in order to carry out an oxidation of carbon monoxide by means of a Pt/AU layer, tests have shown that in a completely surprising manner a carbon monoxide detection can be carried out with a semiconductor gas sensor at temperatures far below 200° C. by means of joining two precious metals platinum and gold.

According to an embodiment, it is advantageous if the adhesion promoter layer contains titanium and has a thickness of less than 300 nm, preferably less than 100 nm, very preferably less than 50 nm. Naturally, the adhesion promoter layer can also be embodied as titanium silicide in order with a carrier of silicon to hereby embody a particularly durable intermediate layer.

In another embodiment, the gold proportion of the alloy of the gas-sensitive layer can lie in a range between 5% and 15%, preferably the proportion is 10%. Tests have shown that in particular with a proportion of 10% gold the semiconductor gas sensor has a surprisingly high sensitivity to carbon monoxide. Furthermore, the sensitivity and reliability of the gas sensor can be increased when a polymer layer, preferably of polymethyl methacrylate, is embodied on the gas-sensitive layer. In particular it is advantageous if the polymer layer has a thickness in the range of 5 nm to 40 nm. Very preferably the polymer layer has a thickness in the range of 10 nm-20 nm.

Furthermore, the gas mixture can comprise one or more of the substances of inert gas, hydrogen, water, carbon dioxide and carbon monoxide. Moreover, it is preferred that the temperature of the gas-sensitive layer and or the gate electrode is in a range between −40° C. and 150° C. In particular a determination of the proportion of carbon monoxide is carried out at a temperature of the gate electrode in a range between −40° C. and 150° C. Accordingly, a preferred use of the semiconductor gas sensor is in the determination of the carbon monoxide content, in particular with a fuel cell.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 3 is a representation of the modulation of the work function of the gas-sensitive layer as a function of the carbon monoxide proportion.

DETAILED DESCRIPTION

Figure 1:
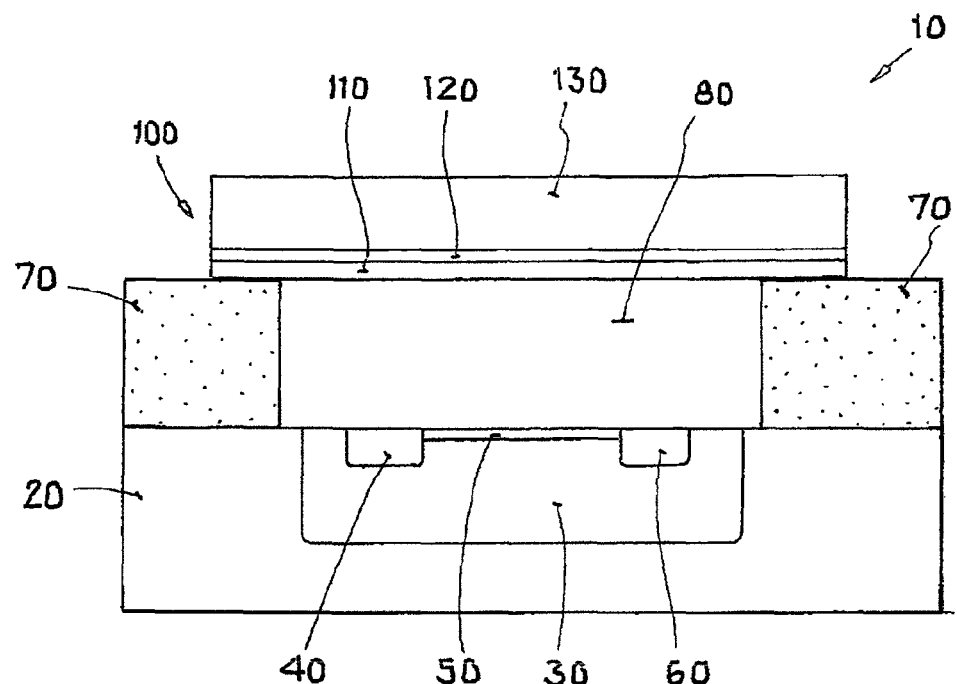
FIG. 1 illustrates an of the semiconductor gas sensor as SGFET in a cross-sectional representation.

The image of FIG. 1 shows a semiconductor gas sensor 10 in a first embodiment as a SGFET, with a semiconductor body 20, a first trough 30 embodied in the semiconductor body 20, a source 40 embodied in the trough 30, a channel region 50 and a drain 60. A spacing layer 70 with a recess 80 is arranged on the semiconductor body. A gap between the channel region 50 and a gate electrode 100, which is also referred to as a suspended gate, arranged on the spacing layer 70 is embodied by means of the recess 80. The gate electrode 100 has a gas-sensitive layer 110 of a platinum gold alloy on the side lying opposite the channel region 50. The gas-sensitive layer 110 is connected by means of an adhesion promoter layer 120 to a semiconductor carrier layer 130 or metallically conductive carrier layer. The gap is connected to a reservoir or the environment—not shown. If a gas or gas mixture, which in addition to other constituents among other things contains carbon monoxide, is now introduced into the gap, the work function of the gas-sensitive layer changes. The conductivity of the channel region is hereby changed by means of influencing a potential depending on the concentration.

Figure 2:
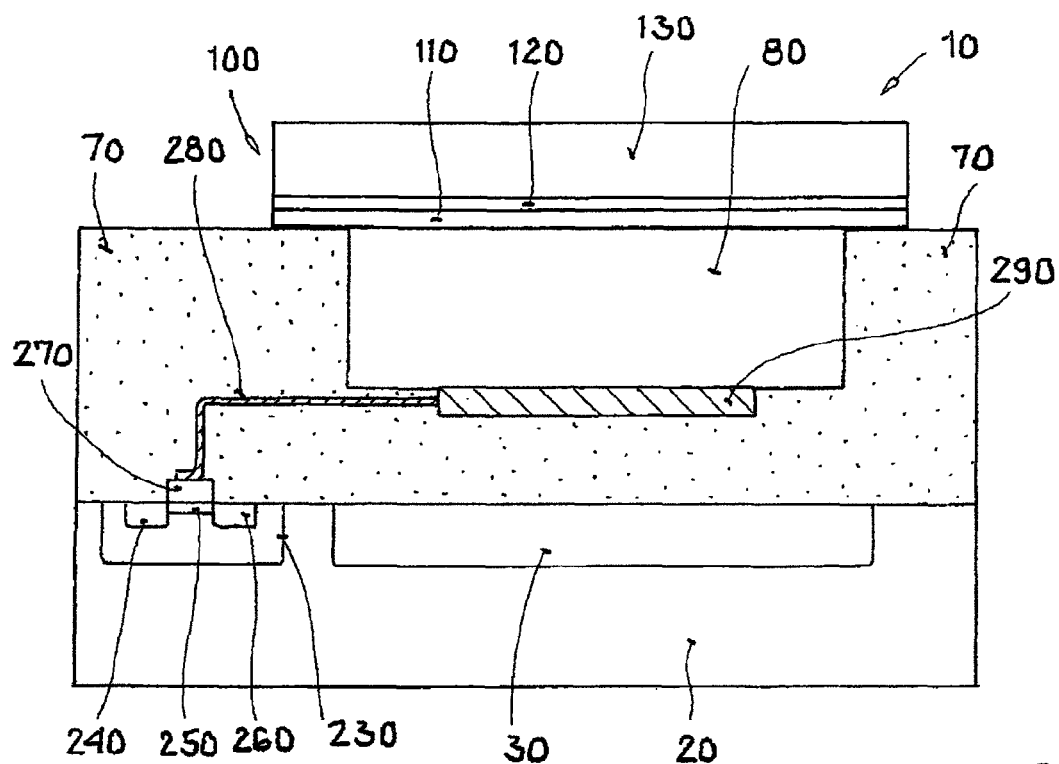
FIG. 2 illustrates an embodiment of the semiconductor gas sensor as a CCFET in a cross-sectional representation.

The image of FIG. 2 shows a second embodiment of the semiconductor gas sensor as a CCFET in a cross-sectional representation. Only the differences from the image in FIG. 1 are explained below. According to the principle of a capacitively controlled FET, the gate electrode 100 operates as a first plate of a capacitor. A source 240, a channel region 250 and a drain 260 are embodied in a second trough 230, wherein the second trough 230 is spatially separated from the first trough 30. A gate 270 is embodied on the channel region 250, wherein the gate 270 is connected by means of a conductor path 280 to a second plate 290. The second plate 290 is embodied in the recess 80, and is arranged at a distance from the gate electrode 100. The spacing layer 70 is embodied below the second plate 190 and covers the second trough 30 from external influences. If carbon monoxide among other things is introduced into the gap, the voltage between the first plate and the second plate 290 changes and hereby the voltage at the gate 270. The conductivity of the channel region 250 is changed hereby depending on the concentration.

FIG. 3 shows a modulation of the work function of the gas-sensitive layer as a function of the carbon monoxide proportion. Only the differences from the previous images are explained below. On the left y-axis in an upper image section the work function WA is plotted and in a lower image section the temperature is plotted. On the x-axis the time t is plotted for both image sections. On the right y-axis for the lower image section in addition the concentration of the proportions of the gas mixture located in the gap is plotted. In the lower image section a quick change over time embodied in a rectangular manner of the carbon monoxide concentration is shown based on a line K1. The slower change over time of a further gas constituent namely H2O is shown by means of a line K2 for a high and a low concentration of hydrogen dioxide. Furthermore, the change of the temperature is shown by means of a line K3, and namely first for a low temperature, subsequently for an average temperature and last for a highest temperature, wherein the highest temperature is in a range between 100° C. and 150° C.

In the upper image section the change over time of the work function as a function of the change of the carbon monoxide concentration and the temperature of the gas-sensitive layer and the concentration of H2O is shown by means of a dashed line WA1 or a solid line WA2. The line WA1 shows the change of the work function for an alloy of approx. 20% gold and 80% platinum, while the line WA2 shows the change of the work function for an alloy of approx. 10% gold and 90% platinum. It is shown that the work function for both alloys changes very quickly and clearly as a function of the carbon monoxide concentration. Furthermore, it is shown that although the one increase in the temperature shifts the position of the lines WA1 and WA2, the sensitivity to a change of the carbon monoxide content remains. Moreover, a change of the H2O concentration has only a slight influence on the modulation of the work function due to the change of the carbon monoxide concentration.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A semiconductor gas sensor comprising:
   a gas-sensitive gate electrode separated by a gap from a channel region and is configured as a suspended gate field effect transistor or the gas-sensitive gate electrode is arranged as a first plate of a capacitor with a gap and a second plate of the capacitor is connected to a gate of the field effect transistor embodied as capacitively controlled; and a semiconductor carrier layer or metallically conductive carrier layer with a bearing adhesion promoter layer and a gas-sensitive layer bearing on the adhesion promoter layer;

wherein a surface of the gas-sensitive layer faces towards the channel region or the second plate, wherein the gate electrode configured as a gas-sensitive layer has a platinum/gold alloy with a gold proportion in a range of 1% to 20% and a polymer layer with a thickness of less than 100 nm and is embodied on the surface of the platinum/gold alloy, and wherein the gap is filled with an oxygen-free gas mixture or a gas mixture with an oxygen proportion of less than 0.1%.

2. The semiconductor gas sensor according to claim 1, wherein the gold proportion is between 5% and 15%.

3. The semiconductor gas sensor according to claim 1, wherein the polymer layer contains polymethyl methacrylate.

4. The semiconductor gas sensor according to claim 1, wherein the polymer layer has a thickness in the range of 5 nm to 15 nm.

5. The semiconductor gas sensor according to claim 1, wherein the gas mixture comprises hydrogen and carbon monoxide.

6. The semiconductor gas sensor according to claim 1, wherein the gate electrode has a temperature between −40° C. and 150° C.

7. A method for measuring a residual gas proportion with a semiconductor gas sensor, the method comprising:

separating a gas-sensitive gate electrode by a gap from a channel region, the gas-sensitive gate electrode being embodied as a suspended gate field effect transistor or the gas-sensitive gate electrode being arranged as a first plate of a capacitor with gap and a second plate of the capacitor being connected to a gate of the field effect transistor embodied as capacitively controlled; and providing a semiconductor carrier layer or metallically conductive carrier layer with a bearing adhesion promoter layer and a gas-sensitive layer bearing on the adhesion promoter layer, a surface of the gas-sensitive layer facing towards the channel region or the second plate, wherein the gas-sensitive layer has a platinum/gold alloy and is embodied with a gold proportion in a range of 1% to 20% and a polymer layer with a thickness of less than 100 nm is embodied on the surface of the platinum/gold alloy, and an oxygen-free gas mixture is fed to the gate electrode and the residual gas proportion is enriched with carbon monoxide and the level of the proportion of carbon monoxide is determined.

8. The method according to claim 7, wherein a determination of the proportion of carbon monoxide is carried out at a temperature of the gate electrode in a range between −40° C. and 150° C.

9. The method according to claim 7, wherein hydrogen is added to the gas mixture.

10. The method according to claim 7, wherein water vapor is added to the gas mixture.

11. The method according to claim 7, wherein the semiconductor gas sensor is adapted to determine a carbon monoxide content with a fuel cell.

* * * * *